United States Patent
Goldberg et al.

(10) Patent No.: US 10,413,392 B2
(45) Date of Patent: *Sep. 17, 2019

(54) APPARATUS AND METHOD FOR THE TREATMENT OF STRESS URINARY INCONTINENCE

(71) Applicant: Boston Scientific Scimed, Inc., Maple Grove, MN (US)

(72) Inventors: Roger P. Goldberg, Evanston, IL (US); Douglas Scherr, Scarsdale, NY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/225,191

(22) Filed: Aug. 1, 2016

(65) Prior Publication Data

US 2016/0338817 A1   Nov. 24, 2016

Related U.S. Application Data

(63) Continuation of application No. 12/182,877, filed on Jul. 30, 2008, now Pat. No. 9,402,705.

(Continued)

(51) Int. Cl.
*A61F 2/00* (2006.01)
*A61B 17/04* (2006.01)
(Continued)

(52) U.S. Cl.
CPC ........ *A61F 2/0045* (2013.01); *A61B 17/0493* (2013.01); *A61B 17/06004* (2013.01);
(Continued)

(58) Field of Classification Search
CPC .......... A61B 17/0493; A61B 17/06004; A61B 17/06066; A61B 17/06109;
(Continued)

(56) References Cited

U.S. PATENT DOCUMENTS 5,097,842 A * 3/1992 Bonn ............... A61B 5/150038
600/575
5,222,974 A 6/1993 Kensey et al.
(Continued)

FOREIGN PATENT DOCUMENTS

EP   1417934 A2   5/2004
EP   1239793 B1   3/2005
(Continued)

OTHER PUBLICATIONS

Office Action for Chinese Application 2,695,212, dated Jun. 1, 2016, 3 pages.

(Continued)

*Primary Examiner* — Christine H Matthews
(74) *Attorney, Agent, or Firm* — Brake Hughes Bellermann LLP

(57) ABSTRACT

An apparatus and method for the treatment of stress urinary incontinence. The apparatus includes a suburethral sling having an adjustment member for adjusting the tension of the sling both during the procedure and post-procedure. The method includes using a needle to simultaneously implant the sling and to deliver a local anesthetic in the groin area while implanting the sling.

21 Claims, 13 Drawing Sheets

Related U.S. Application Data

(60) Provisional application No. 60/952,802, filed on Jul. 30, 2007.

(51) Int. Cl.
*A61B 17/06* (2006.01)
*A61M 19/00* (2006.01)
*A61B 17/00* (2006.01)

(52) U.S. Cl.
CPC .. *A61B 17/06066* (2013.01); *A61B 17/06109* (2013.01); *A61M 19/00* (2013.01); *A61B 2017/00004* (2013.01); *A61B 2017/00438* (2013.01); *A61B 2017/00805* (2013.01); *A61B 2017/06076* (2013.01); *A61F 2250/0007* (2013.01)

(58) Field of Classification Search
CPC .......... A61B 2017/00004; A61B 2017/00438; A61B 2017/00805; A61F 2250/0007; A61F 2/0045; A61M 19/00
See application file for complete search history.

(56) References Cited

U.S. PATENT DOCUMENTS

| | | | |
|---|---|---|---|
| 5,658,299 A | 8/1997 | Hart | |
| 5,842,478 A | 12/1998 | Benderev et al. | |
| 5,964,806 A | 10/1999 | Cook et al. | |
| 6,045,498 A | 4/2000 | Burton et al. | |
| 6,419,624 B1 | 7/2002 | Burton et al. | |
| 6,419,701 B1 | 7/2002 | Cook et al. | |
| 6,502,578 B2 | 1/2003 | Raz et al. | |
| 6,579,224 B1 | 6/2003 | Burton et al. | |
| 6,612,977 B2 | 9/2003 | Staskin et al. | |
| 6,645,138 B2 | 11/2003 | Cook et al. | |
| 6,652,450 B2 | 11/2003 | Neisz et al. | |
| 6,691,711 B2 | 2/2004 | Raz et al. | |
| 6,702,827 B1 | 3/2004 | Lund et al. | |
| 6,881,184 B2 | 4/2005 | Zappala | |
| 6,911,002 B2 | 6/2005 | Fierro et al. | |
| 6,932,759 B2 | 8/2005 | Ulmsten et al. | |
| 6,971,986 B2 | 12/2005 | Westrum et al. | |
| 7,014,606 B2 | 3/2006 | Burton et al. | |
| 7,083,568 B2 | 8/2006 | Porter et al. | |
| 7,083,598 B2 | 8/2006 | Liska et al. | |
| 7,198,597 B2 | 4/2007 | Arnal et al. | |
| 7,204,802 B2 | 4/2007 | De et al. | |
| 8,834,350 B2 * | 9/2014 | Chapman | A61B 17/0401 600/29 |
| 9,402,705 B2 * | 8/2016 | Goldberg | A61B 17/0493 |
| 2002/0016567 A1 * | 2/2002 | Hochman | A61M 5/1456 604/131 |
| 2002/0091373 A1 | 7/2002 | Berger | |
| 2002/0107430 A1 | 8/2002 | Neisz et al. | |
| 2002/0151763 A1 | 10/2002 | Cook et al. | |
| 2002/0156342 A1 | 10/2002 | Burton et al. | |
| 2002/0169420 A1 | 11/2002 | Galt et al. | |
| 2002/0183588 A1 | 12/2002 | Fierro | |
| 2003/0023136 A1 | 1/2003 | Raz et al. | |
| 2003/0045774 A1 * | 3/2003 | Staskin | A61B 17/0401 600/29 |
| 2003/0065402 A1 | 4/2003 | Anderson et al. | |
| 2004/0015045 A1 | 1/2004 | Burton et al. | |
| 2004/0215054 A1 | 10/2004 | Siegel et al. | |
| 2004/0231678 A1 | 11/2004 | Fierro et al. | |
| 2004/0249240 A1 | 12/2004 | Goldmann et al. | |
| 2005/0004576 A1 | 1/2005 | Benderev | |
| 2005/0021086 A1 | 1/2005 | De Leval | |
| 2005/0027161 A1 | 2/2005 | Cook et al. | |
| 2005/0055104 A1 | 3/2005 | Arnal et al. | |
| 2005/0107805 A1 | 5/2005 | Bouffier et al. | |
| 2005/0143618 A1 | 6/2005 | Anderson et al. | |
| 2005/0256364 A1 | 11/2005 | Burton et al. | |
| 2005/0283040 A1 | 12/2005 | Greenhalgh | |
| 2006/0009673 A1 | 1/2006 | Chan | |
| 2006/0025798 A1 | 2/2006 | Cook et al. | |
| 2006/0089525 A1 | 4/2006 | Mamo et al. | |
| 2006/0089669 A1 | 4/2006 | Schreiner et al. | |
| 2006/0173468 A1 | 8/2006 | Simmon et al. | |
| 2006/0183966 A1 | 8/2006 | Neisz et al. | |
| 2006/0195007 A1 | 8/2006 | Anderson et al. | |
| 2006/0195010 A1 | 8/2006 | Arnal et al. | |
| 2006/0195013 A1 | 8/2006 | Gellman et al. | |
| 2006/0199996 A1 | 9/2006 | Caraballo et al. | |
| 2006/0217655 A1 | 9/2006 | Vitullo et al. | |
| 2006/0235262 A1 | 10/2006 | Arnal et al. | |
| 2006/0241339 A1 | 10/2006 | Cook et al. | |
| 2006/0259006 A1 | 11/2006 | McKay et al. | |
| 2006/0260618 A1 | 11/2006 | Hodroff et al. | |
| 2006/0281964 A1 | 12/2006 | Burton et al. | |
| 2006/0287571 A1 | 12/2006 | Gozzi et al. | |
| 2007/0021686 A1 | 1/2007 | Gellman et al. | |
| 2007/0049790 A1 | 3/2007 | Wagner et al. | |
| 2007/0068538 A1 | 3/2007 | Anderson et al. | |

FOREIGN PATENT DOCUMENTS

| | | |
|---|---|---|
| EP | 1229857 B1 | 12/2005 |
| EP | 1665991 A2 | 6/2006 |
| EP | 996389 B1 | 2/2008 |
| EP | 1399082 B1 | 10/2008 |
| EP | 1189552 B1 | 4/2009 |
| WO | 9835632 A1 | 8/1998 |
| WO | 9856311 A1 | 12/1998 |
| WO | 0066030 A1 | 11/2000 |
| WO | 0074633 A2 | 12/2000 |
| WO | 0102027 A1 | 1/2001 |
| WO | 0126581 A1 | 4/2001 |
| WO | 0145589 A1 | 6/2001 |
| WO | 0226108 A2 | 4/2002 |
| WO | 02098301 A1 | 12/2002 |
| WO | 03002027 A1 | 1/2003 |
| WO | 2004017862 A2 | 3/2004 |
| WO | 2004034912 A1 | 4/2004 |
| WO | 2004096087 A1 | 11/2004 |
| WO | 2005023152 A1 | 3/2005 |
| WO | 2005082276 A1 | 9/2005 |
| WO | 2005110243 A2 | 11/2005 |
| WO | 2006046950 A1 | 5/2006 |
| WO | 2006084167 A1 | 8/2006 |
| WO | 2006091786 A1 | 8/2006 |
| WO | 2007002071 A1 | 1/2007 |
| WO | 2007017712 A1 | 2/2007 |
| WO | 2007059368 A1 | 5/2007 |
| WO | 2007066169 A1 | 6/2007 |

OTHER PUBLICATIONS

"AMS Solutions for Life", Monarc Overview—Monarc Subfascial Hammock, 2007, 2 pages.
U.S. Appl. No. 12/182,877, Office Action Response filed May 20, 2013, 6 pages.
AU Application Serial No. 2008282204, Examination Report dated May 12, 2013, 8 pages.
JP Application Serial No. 2010-520157, Office Action dated Nov. 21, 2013, 7 pages.
JP Application Serial No. 2010-520157, Final Office Action dated May 13, 2013, 2 pages.
JP Application Serial No. 2010-520157, Response to Final Office Action filed Sep. 11, 2013, 5 pages.
"Bard Products for the Treatment of Stress Urinary Incontinence", 2009, 1 page.
U.S. Appl. No. 12/182,877, Advisory Action dated Feb. 20, 2015, 3 pages.
U.S. Appl. No. 12/182,877, Final Office Action dated Dec. 10, 2014, 15 Pages.
U.S. Appl. No. 12/182,877, Final Office Action dated Sep. 28, 2015, 11 pages.
U.S. Appl. No. 12/182,877, Non-Final Office Action dated Mar. 12, 2015, 12 pages.

(56) References Cited

OTHER PUBLICATIONS

U.S. Appl. No. 12/182,877, Notice of Allowance dated Apr. 6, 2016, 9 Pages.
U.S. Appl. No. 12/182,877, Notice of Allowance dated Dec. 9, 2015, 8 Pages.
Response to Final Office Action for U.S. Appl. No. 12/182,877, filed Nov. 25, 2015, 5 pages.
Response to Final Office Action for U.S. Appl. No. 12/182,877, filed Sep. 3, 2014, 7 pages.
Response to Final Office Action for U.S. Appl. No. 12/182,877, filed Feb. 6, 2015, 7 pages.
U.S. Appl. No. 12/182,877, Non-Final Office Action dated Jun. 12, 2014, 10 pages.
CA Application No. 2,695,212, Office Action dated Jul. 10, 2014, 2 Pages.
American Medical Systems, "About AdVance", 4 pages.
AMS Solution for Life, Investors, American Medical Systems Signs Cross-Licensing Agreement with Caldera Medical; Patent Litigation Suit Dismissed Under Separate Agreement, retrieved from http://phx.corporate-ir.net/phoenix.zhtml?c=122198&p=irol-newsArticle&ID=878930&hi . . . , downloaded on Jun. 22, 2007, 2 pages.
AMS Solution for Life, "American Medical Systems-Financial Release", Investors, American Medical Systems and Boston Scientific Corporation Announce Litigation Settlement, retrieved from http://phx.corporate-ir.net/phoenix.zhtml?c=122198&p=irol-newsArticle_Print&ID=14913 . . . , downloaded on Jun. 22, 2007, 1 page.
Boston Scientific, "Obtryx® Transobturator Mid-Urethral Sling System", retrieved from http://www.bostonscientific.com/med_specialty/deviceDetail.ips?task=tskBasicDevice.isp, downloaded on Jul. 13, 2007, 1 page.
CA Application No. 2,695,212, Office Action dated May 26, 2015, 5 pages.
CA Application No. 2,695,212, Office Action Response Filed Jan. 7, 2015, 11 pages.
CA Application No. 2,695,212, Office Action Response filed Nov. 23, 2015, 4 pages.
EP Application No. 08796887.1, Examination Notification Art. 94(3) mailed May 15, 2014, 7 pages.
Supplemental European Search Report for EP Application No. 08796887.1, dated Oct. 29, 2013, 6 pages.
EP Application No. 08796887.1, Examination Notification Art. 94(3) Response filed Sep. 23, 2014, 10 Pages.
Ethicon, "Women's Health & Urology—GYNECARE TVT SECUR* System", 2008, 3 pages.
Ethicon, "Women's Health & Urology—GYNECARE TVT, Tension-Free Support for Incontinence", 2008, 2 pages.
Promedon, "Male Sling Protocol Rev 04 Clinical Study for ARGUS Adjustable Male Sling", retrieved from http:// www.itcmedical.net/argus/argus_protocolo_male_sling.pdf, Aug. 6, 2003, 14 pages.
Romano, et al., "An adjustable male sling for treating urinary incontinence after prostatectomy: a phase III multicentre trial", Oct. 4, 2005, 7 pages.
Communication pursuant to Article 94(3) EPC for European Application No. 08796887.1, mailed Dec. 21, 2017, 5 pages.

* cited by examiner

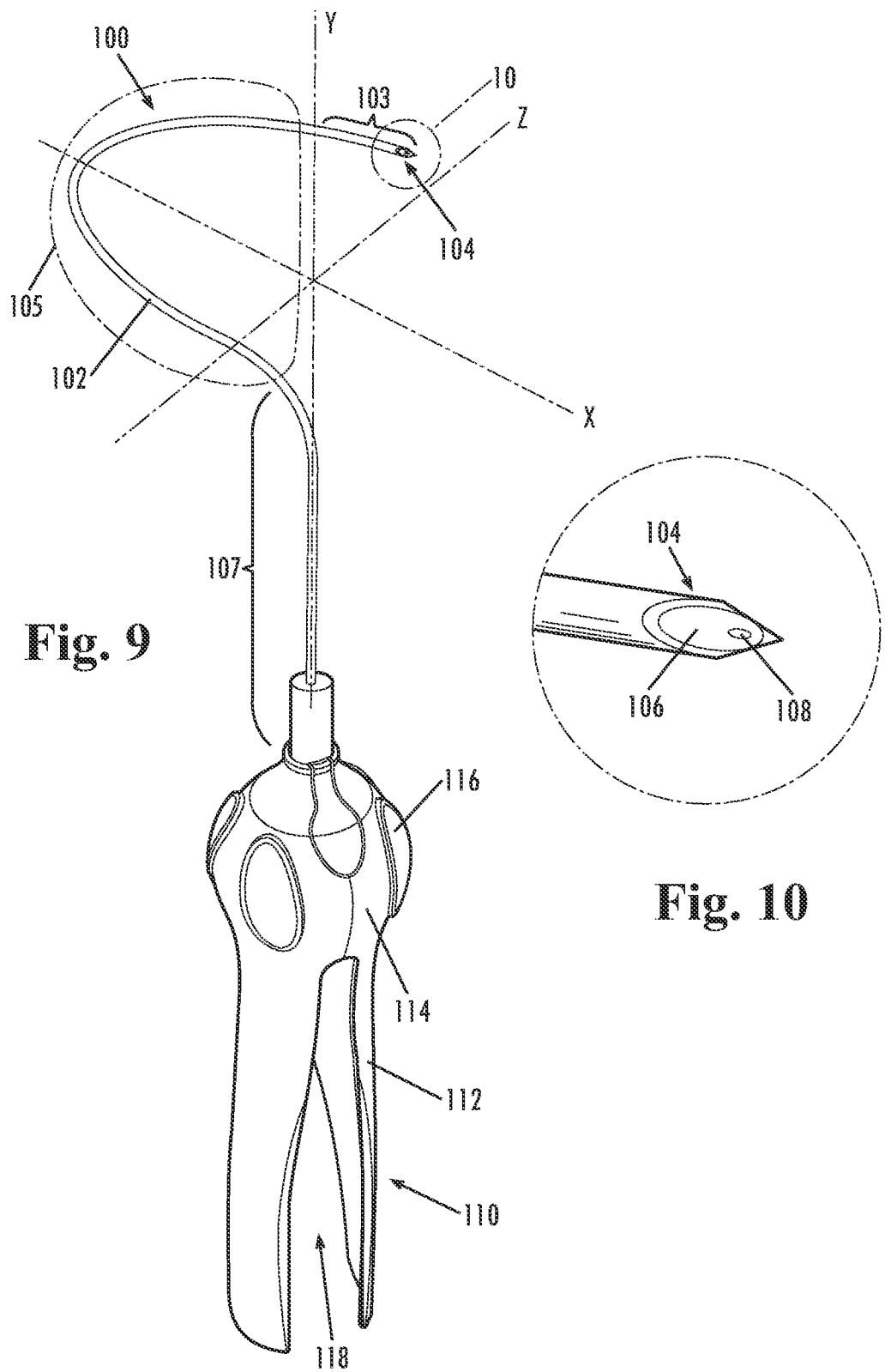

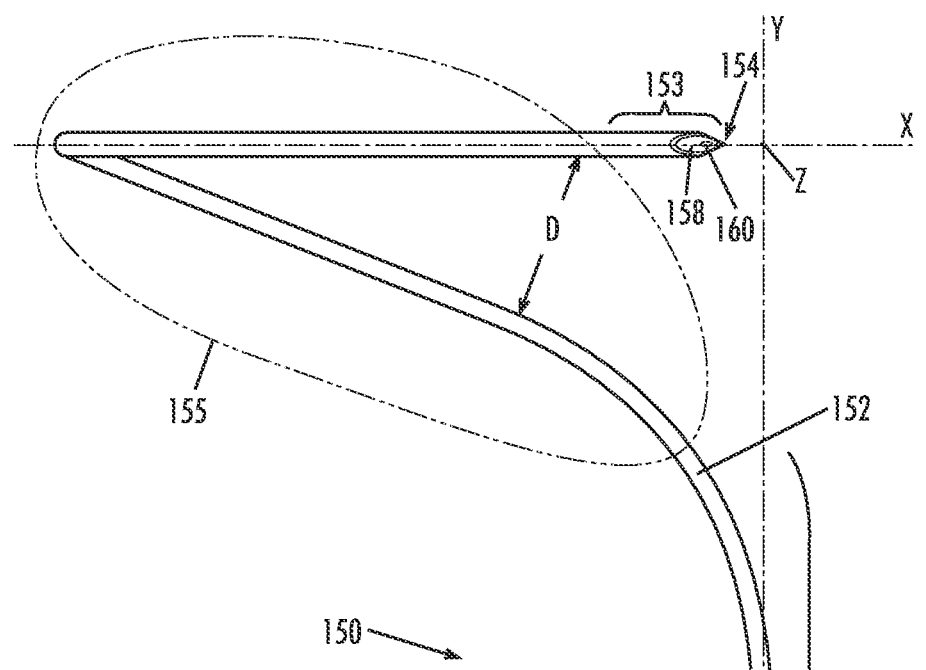
Fig. 12
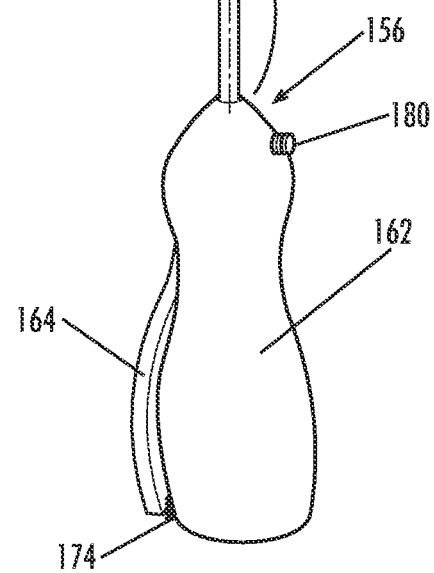

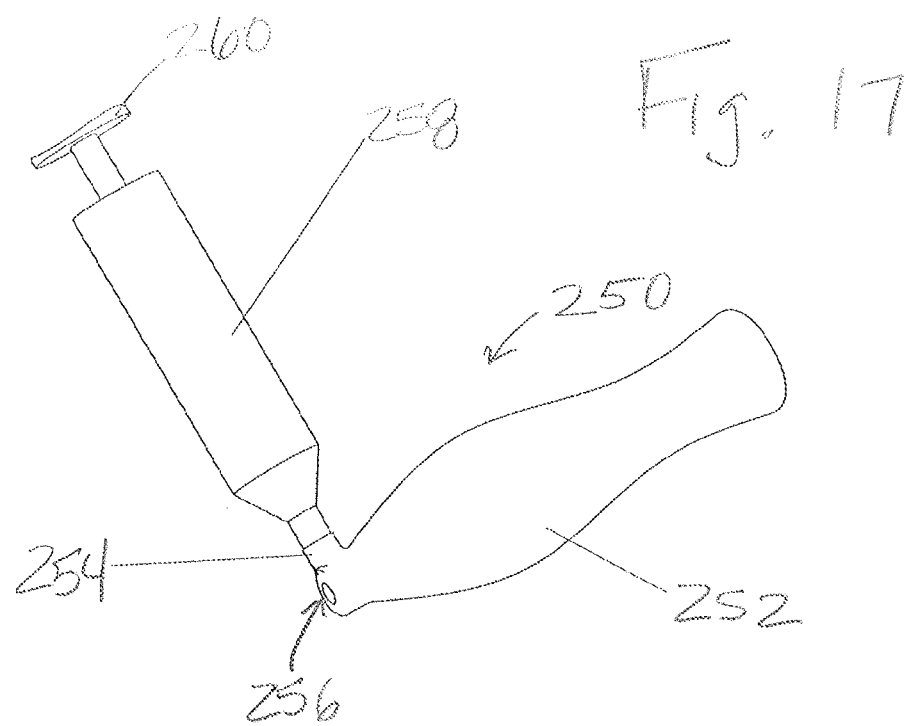
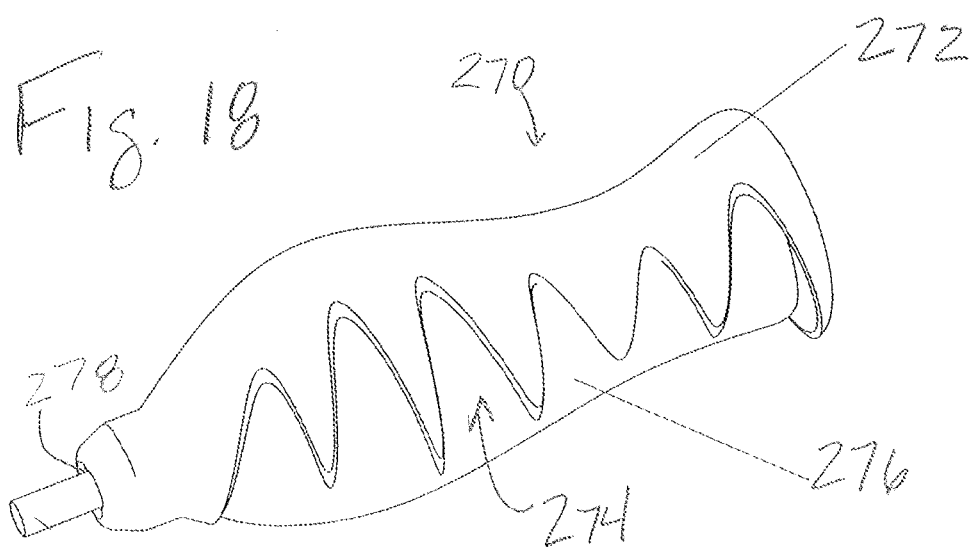

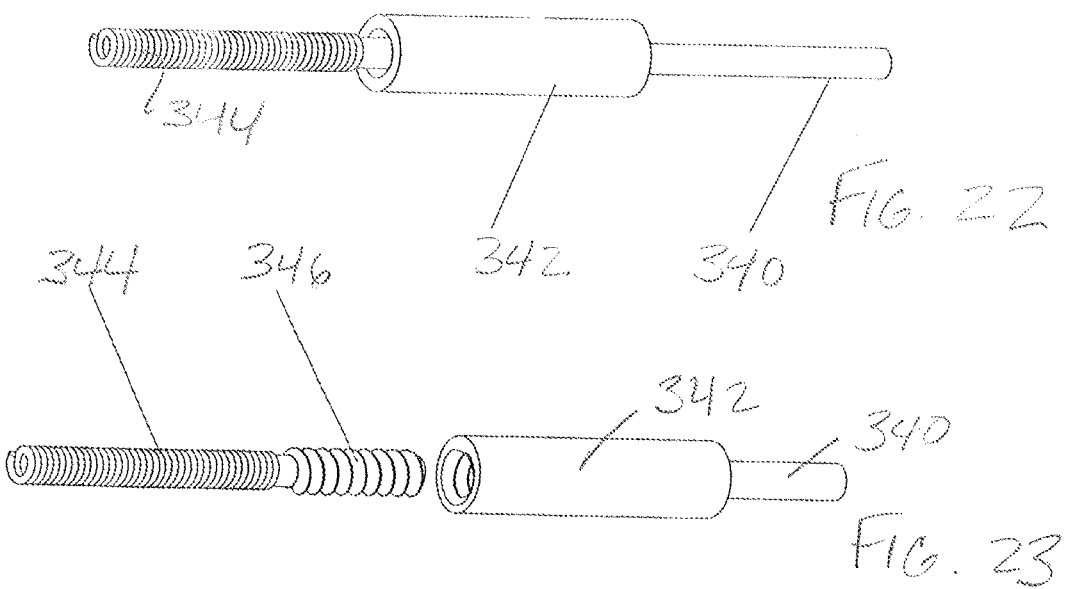
FIG. 22
FIG. 23
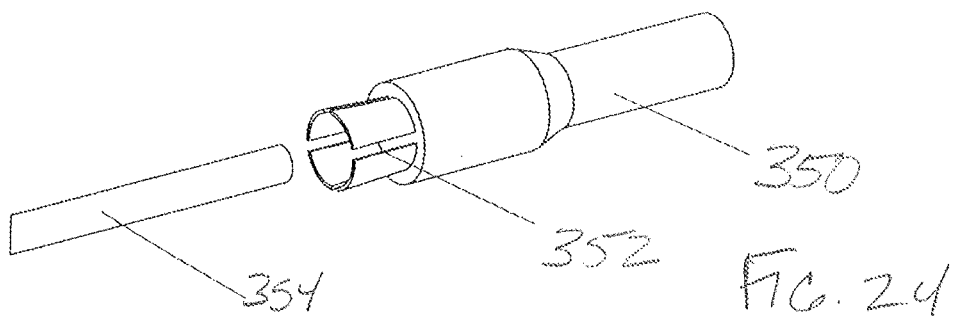
FIG. 24
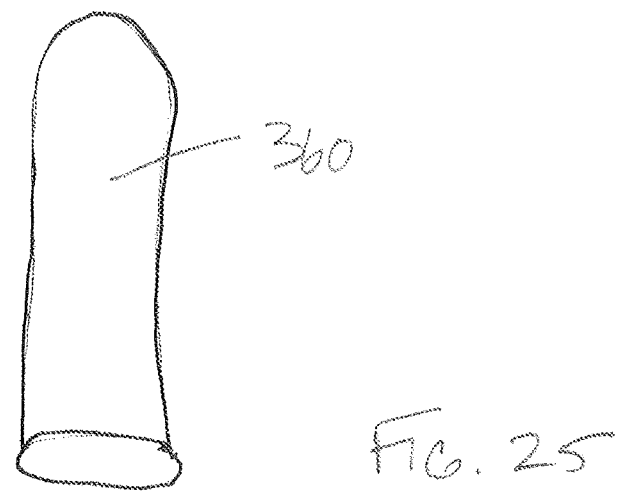
FIG. 25

APPARATUS AND METHOD FOR THE TREATMENT OF STRESS URINARY INCONTINENCE

CROSS-REFERENCE TO RELATED APPLICATIONS

This application is a Continuation of, and claims priority to, U.S. patent application Ser. No. 12/182,877, filed on Jul. 30, 2008, entitled "APPARATUS AND METHOD FOR THE TREATMENT OF STRESS URINARY INCONTINENCE", which, in turn, claims priority to U.S. Patent Application No. 60/952,802, filed on Jul. 30, 2007, the disclosures of which are incorporated by reference herein in their entirety.

FIELD OF THE INVENTION

The present invention relates generally to the field of medical devices, and in particular to an apparatus and method for treating stress urinary incontinence in a human or animal subject.

BACKGROUND OF THE INVENTION

Stress urinary incontinence ("SUI") is a widespread problem throughout the world affecting people of all ages and gender. SUI is the involuntary leakage of small amounts of urine resulting from an increased pressure in the abdomen and may result while sneezing, coughing, laughing, bending, lifting, etc. While primarily a female problem, men also suffer from stress urinary incontinence, and rates of male SUI are increasing along with the increased use of prostate surgery. Stress incontinence in men is typically the result of a weakened urethral sphincter that surrounds the prostate, frequently as a result of prostate surgery.

For treating SUI, it is often necessary to resort to surgery. Conventional techniques consist of restoring the natural mechanisms of continence, maintaining the urethra in the abdominal cavity, and/or increasing urethral resistance. To do this, a conventional sling is placed under the urethra, thereby making it possible to improve the suspension and provide some compression of the urethra. Currently, there are a variety of different sling procedures which differ in the anchoring methods and materials used.

Despite advances in midurethral sling design over the past years, there still remains considerable room for improvements, particularly in sling design and placement. For example, such procedures typically require hospitalization. Thus, many females and males with stress urinary incontinence avoid or delay undergoing an operation. Moreover, although serious complications associated with sling procedures are infrequent, they do occur. In some cases, the slings cause friction in the area of the vagina or urethra during the patient's movements and may injure different organs with which they are in contact. This friction may then cause erosion, inflammation or infection, or even cause rejection of the sling, thereby requiring another operation to surgically remove the sling.

Other shortcomings of known sling designs include the fact that multiple incisions are typically required to implant a sling, thereby increasing the patient's level of discomfort and recovery time. Additionally, passage of mesh through the skin or subcutaneous tissue can result in patient discomfort and therefore most commonly requires general anesthesia. Moreover, once implanted, the sling cannot be adjusted, and thus if the sling is not implanted in the precise or ideal location, the patient may continue to have incontinence-related issues. There are some devices whose use compromises the surgeon's ability to easily and accurately tension the sling. This is being perceived as a major shortcoming, and is probably a major reason underlying unacceptable initial failure rates of approximately 25%.

Accordingly, there exists a need for a sling that satisfactorily treats stress urinary incontinence and that permits post-operative adjustment of the sling. Further needs exist for methods for implanting slings that minimize a subject's discomfort and recovery time and allow for placement under local anesthesia.

SUMMARY OF THE INVENTION

Advantageously, the present invention provides an adjustable sling (or a 'mini sling' having minimal mesh arms traveling though hidden anatomic spaces) for treating stress urinary incontinence in both female and male subjects. Notably, a practitioner can implant the sling in an office or other ambulatory setting using a local anesthetic rather than using general anesthesia in a hospital setting. Such implantation can be achieved, in the female, by passing the needle from a vaginal incision out to either the groin area ("inside out transobturator" approach), or suprapubic region ("inside-out retropubic" approach). In the male, such implantation can be achieved by passing the needle from a perineal incision out to the groin area ("inside-out transobturator approach"), which before now has not been described or performed in male subjects. Also advantageously, the sling of the present invention can be adjusted both during the procedure and at a future a date without further surgery, incisions, or puncture wounds. Since the subject is awake (and not under general anesthesia), the tension of the sling can be adjusted while the patient coughs (or engaged in another activity that causes intraabdominal pressure). Additionally, if the sling is not performing optimally, the practitioner can adjust the tension days after the procedure.

In a first form, the present invention provides an apparatus for the treatment of stress urinary incontinence. The apparatus includes a sling body having an intermediate portion and two end portions and a suture, wherein the suture extends through the sling body. The suture further provides an adjustment loop proximate to the intermediate portion for postoperative adjustment. Preferably, the sling is body is sized and shaped so at to minimize excess body from spanning through anatomical spaces where it not needed for the treatment of incontinence.

In another form, the present invention provides a needle delivery device for implanting a medical device for the treatment of stress urinary incontinence. The needle delivery device has a needle body, wherein the needle body includes an aperture configured to receive a suture end of the medical device, and a lumen extending through the length of the needle body, wherein the lumen is adapted to deliver a fluid therethrough. Accordingly, in use, the needle delivery device can simultaneously deliver a local anesthesia while implanting the medical device through a precise anatomic pass with the needle body.

In yet another form, the present invention provides a method for implanting a medical device to treat urinary incontinence in a human or animal subject. The method includes the steps of making an incision in the vaginal or perineal area; inserting first and second needles into the human or animal subject; guiding the needles to the appropriate area in the groin or suprapubic area while simultaneously injecting a local anesthetic with the needles; removing the needles; positioning the sling; and leaving at least a portion of the sling (such as the tensioning suture) accessible for post-operative adjustment of the sling.

In another form, the present invention provides a kit for the treatment of urinary incontinence. The kit includes a suburethral sling, a pair of needle delivery devices, wherein each needle delivery device is configured to simultaneously deliver local anesthesia and implant the sling around the urethra, and a finger guard.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWINGS

FIG. 9 depicts a perspective view of a needle delivery device for delivering a sling according to an example embodiment of the present invention.

FIG. 10 depicts a detailed view of the tip of the needle delivery device of FIG. 9.

FIG. 12 depicts a perspective view of a needle delivery device for delivering a sling according to another example embodiment of the present invention.

FIG. 17 depicts a perspective view of a handle for a needle delivery device of the present invention according to another example embodiment.

FIG. 18 depicts a perspective view of a handle for a needle delivery device of the present invention according to yet another example embodiment.

FIGS. 22 and 23 depict perspective views of a guidewire and suture end of a sling according to another example embodiment of the present invention.

FIG. 24 depicts a perspective view of a guidewire and suture end of a sling according to yet another example embodiment of the present invention.

FIG. 25 depicts a finger guard according to an example embodiment of the present invention for use with a needle of the present invention.

DETAILED DESCRIPTION OF EXAMPLE EMBODIMENTS

The present invention may be understood more readily by reference to the following detailed description of the invention taken in connection with the accompanying drawing figures, which form part of this disclosure. It is also understood that this invention is not limited to the specific devices, methods and conditions or parameters described and/or shown herein, and that the terminology used herein is for the purpose of describing particular embodiments by way of example only and is not intended to be limiting of the claimed invention. Also, as used in the specification including the appended claims, the singular forms "a", "an" and "the" include the plural, and reference to a particular numerical value indicates at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about", it will be understood that the particular value forms another embodiment.

The present invention provides a sling for treating incontinence and an apparatus for delivering the sling around a subject's urethra while at the same time delivering local anesthesia along the tissue tract through which the sling is delivered.

Figure 1:
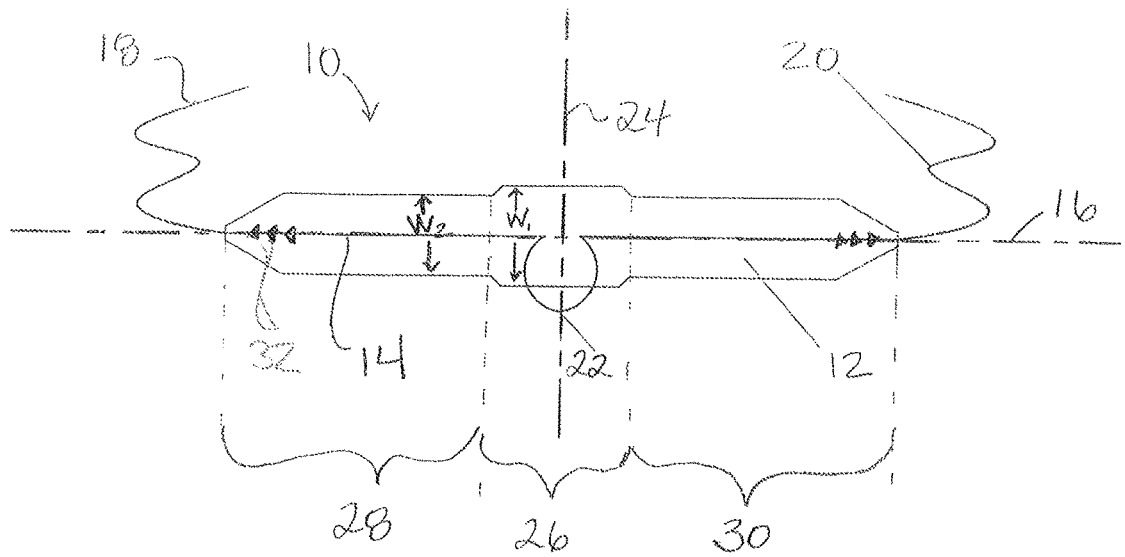
FIG. 1 depicts a front view of a sling in accordance with a first example embodiment of the present invention.

Referring now to the figures, FIG. 1-8 depict slings of the present invention according to various example embodiments. As shown in FIG. 1, the sling 10 includes a flexible body 12 having a single suture 14 extending or woven through the body generally along the sling's longitudinal axis 16. The suture 14 can be affixed to or formed as part of the body 12. The suture includes ends 18, 20 extending from lateral sides of the body 12 and an intermediate loop portion 22. The ends 16, 18 are configured to secure the sling 10 in the subject as well as to adjust the tension of the sling. The loop 22 also is configured to aid the practitioner in adjusting the tension of the sling 10 when it is implanted and post-operatively. Although a single suture is discussed herein, a plurality of sutures can be used and be within the scope of the present invention. In such instances, the sutures can extend from a point near the lateral edges of the body or multiple sutures can extend through the length of the body. Preferably, the suture 14 is constructed of a bioabsorbable material such as but not limited to PGA, PDS, PLGA, VICRYL™, and catgut. A bioabsorbable suture absorbs in the subject's body and avoids an additional visit to the practitioner to remove the sutures. Alternatively, the suture 92 can be constructed of a non-absorbable biocompatible material and removed at a future date (or not removed at all).

Preferably, the body 12 of the sling 10 is symmetrically shaped about both its longitudinal axis 16 and its transverse axis 24. As shown, the body 12 has an intermediate or suburethral portion 26 and two end (or periurethral) portions 28, 30. The intermediate portion 26 has a generally elongated hexagonal like shape (i.e., elongated along the longitudinal axis 16), while the end portions 28, 30 are strip-like and taper to a width that is slightly larger than or the same size as the diameter of the suture 14. In alternative embodiments, the size and shape of the sling can vary. For example, the intermediate portion can have a tapered oval shape (i.e., tapered in the direction along the longitudinal axis). Additionally, it may be advantageous to implant a longer sling in a male subject and shorter sling in a female subject. However generally, the widths are approximately the same regardless of whether the sling is implanted in a male or female subject. For example, the width $W_1$ of the intermediate portion can be approximately 10 mm to 40 mm. The widths $W_2$ of the end strips can be approximately 5 mm to 10 mm. Advantageously, this construction minimizes the amount of the sling body that is located in the anatomical spaces of the subject. For a sling to be implanted in a female subject, the length of the body can be between approximately 3 cm to 13 cm, and preferably around 8 cm, with the intermediate portion approximately 3-5 cm long. For a sling to be implanted in a male subject, the length of the body can be between approximately 12 cm to 22 cm, and preferably around 16 cm with the intermediate portion approximately 8-12 cm long. As shown, the end strips taper at their lateral ends to a few millimeters, such as between about 3 mm to 30 mm, and more preferably around 5 mm.

The body 12 is preferably constructed from a sheet-like material. Preferably, the sheet-like material comprises a biocompatible, surgical mesh material such as polypropylene, that does not absorb in the subject's body. Other exemplary biocompatible mesh materials include nylon, polyester, and polytetrafluoroethylene. In such embodiments utilizing mesh, the sling 10 is held in appropriate placement in the subject's body by the friction between the sling and the surrounding tissue. The subject's body forms scar tissue around and through the mesh body, thereby further securely holding the mesh body in place. However, other suitable biocompatible materials, including "non-mesh" materials can be used as well. Alternatively, bioabsorbable materials such as polyglycolic acid, polylactic acid, PEA, PEUR, PEG, and PLLA can be employed.

Advantageously, when implanted in a human or animal subject, the sling body preferably does not extend through the subject's skin. Rather, only the suture ends (which eventually absorb into the body) temporarily extend through the patient's skin to thereby allow retensioning at a future date. Accordingly, since the overall size of the sling body is reduced and therefore does not extend into anatomical spaces where it provides no additional benefits for the treatment of incontinence, patient discomfort is significantly reduced.

Figure 2:
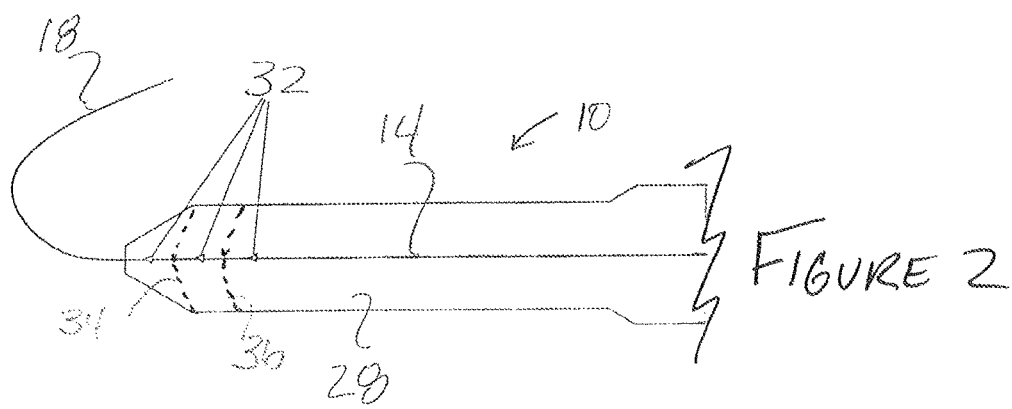
FIG. 2 depicts a front view of an end portion of the sling of FIG. 1.
Figure 3:
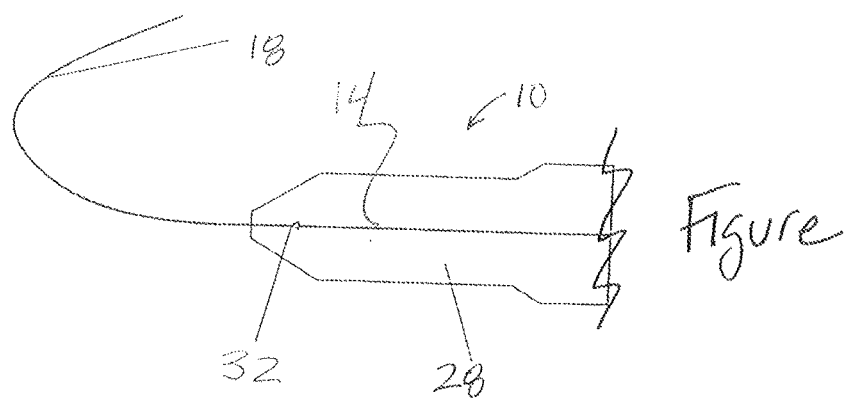
FIG. 3 depicts a front view of a modified end portion of the sling of FIG. 1.

Optionally, the sling body 12 can be constructed of a single size and shape that can be trimmed to an appropriate size and shape. The sling body 10 has one or more sutures 14 secured at multiple points along the body 12 of the sling. For example, the suture 14 can be attached to the body 12 of the sling 10 (e.g., mesh sling) with multiple knots 32. The plurality of knots 32 securing the suture 14 to the body 12 prevents the suture from detaching from the sling body when the body is cut. For example, FIGS. 1 and 2 depict end strips 28 of the sling 10 having three such knots 32. Accordingly, the practitioner can cut the sling body 12, such as in the areas of lines 34 or 36, thereby removing segments of the mesh body, to an appropriate size without detaching the suture 14 from the sling 10, so as to achieve the size shown in FIG. 3. The suture 14 can be tied (or otherwise secured) to the sling body with any suitable number of knots. Thus, the practitioner can cut the sling body to any suitable size and shape without disengaging the suture from the body.

Figure 4:
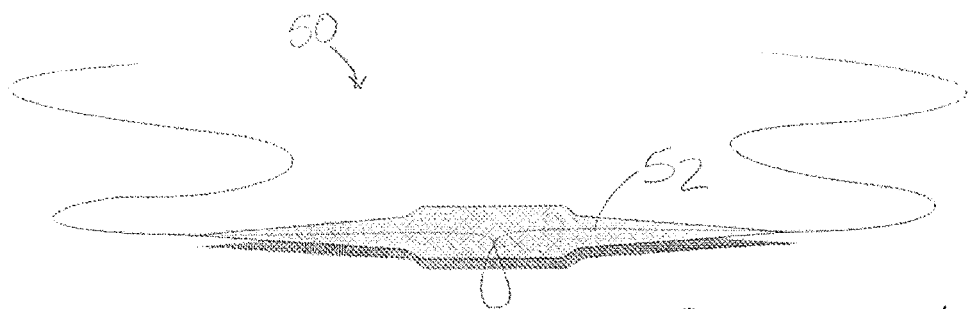
FIG. 4 depicts a perspective view of a sling in accordance with a second example embodiment of the present invention.
Figure 5:
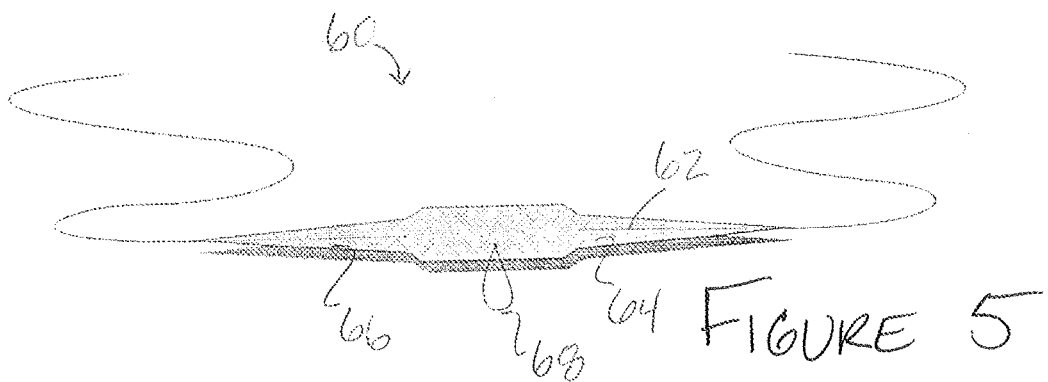
FIG. 5 depicts a perspective view of a sling in accordance with a third example embodiment of the present invention.

FIGS. 4-8 show additional sling embodiments. For example, FIGS. 4 and 5 show slings 50, 60 having substantially the same size and shape as that of FIG. 1, but the end strip portions taper from the intermediate portion to a tip that is the same size as or slightly larger than the diameter of the suture ends. The notable difference between FIGS. 4 and 5 is that in FIG. 4, the suture 52 is woven through the length of the body 54, while in FIG. 5, the suture 62 is woven through end strips 64, 66 of the body, but at the suture extends across an external face of the intermediate portion with its loop 68 extending through an opening and protruding from the opposite face. Otherwise, the slings 50, 60 are substantially similar to that of FIGS. 1-3, but with the differences noted above.

Figure 6:
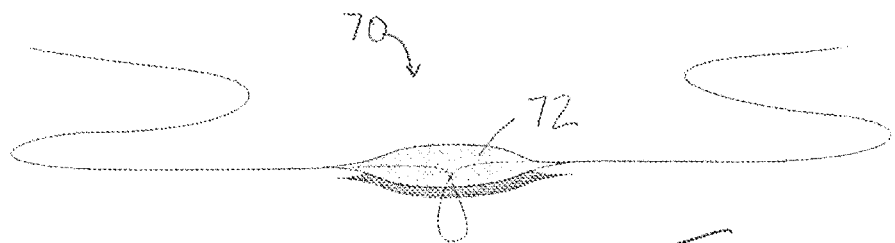
FIG. 6 depicts a perspective view of a sling in accordance with a fourth example embodiment of the present invention.

FIG. 6 depicts a sling 70 according to another example embodiment. The sling 70 is substantially similar to that of FIGS. 1-5, but with the differences noted herein. In this embodiment, the body 72 smoothly tapers to its lateral ends in a manner somewhat like the shape of a teardrop.

Figure 7:
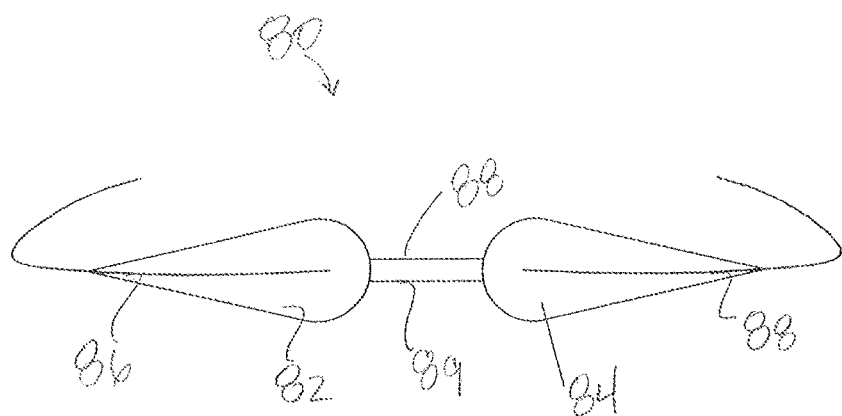
FIG. 7 depicts a front view of a sling in accordance with a fifth example embodiment of the present invention.

FIG. 7 depicts a sling 80 according to yet another example embodiment. The sling 80 is substantially similar to that of FIGS. 1-6, but with the differences noted herein. In this embodiment, the body has generally a two-piece construction having first and second spaced-apart members 82, 84. As depicted a first suture 86 is affixed to or formed as part of the first member 82, and a second suture 86 is affixed to or formed as part of the second member 84. The first and second members 82, 84 are connected by at least one and preferably two sutures 88, 89. Preferably, the two sutures 88, 89 connecting the first and second members 82, 84 are not bioabsorbable. Alternatively, the two sutures 88, 89 connecting the first and second members 82, 84 can be constructed of a bioabsorbable material. Also preferably, the first and second members 82, 84 are spaced apart a sufficient distance such that once implanted in a human or animal subject, the first and second members are not placed beneath the urethra of subject, but rather are placed towards the sides (in the periurethral space). Even though the first and second members 82, 84 are depicted as generally elongated triangular-like shapes with rounded base portions, any suitably sized and shaped members can be employed.

Figure 8:
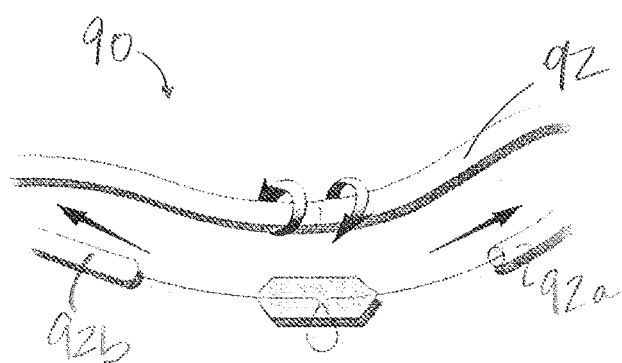
FIG. 8 depicts a perspective view of a sling in accordance with a sixth example embodiment of the present invention.

FIG. 8 depicts a sling 90 according to yet another example embodiment. The sling 90 is substantially similar to that of FIGS. 1-7, but with the differences noted herein. The sling includes a sheath 90 (or tubing) that covers and protects the body of the sling during implantation (i.e., passage through a needle body). The sheath 92 is the removed in two parts 92a, 92b, thereby exposing the sling body and allowing for final tensioning and positioning.

As shown in FIGS. 9-18, a needle delivery device can be used to implant a sling of the present invention in appropriate placement around the urethra while also delivering a sufficient amount of fluid, such as a local anesthetic (e.g., lidocaine). Preferably, a pair of needle delivery devices is used simultaneously and manipulated independently of each other. The two needle delivery devices are substantially similar to one another and preferably are mirror images of one another, and thus, only one needle delivery device of the pair will be discussed in detail herein. Thus, the practitioner would use the appropriate one of the needle delivery devices in his left hand and the other in his right hand. As discussed below, the needle delivery device can include a variety of shapes including, arcuate, curved, spiral, helical, or straight.

Advantageously, the practitioner makes "one pass" with the needle bodies of the needle delivery devices. In other words, the practitioner advances the needle bodies into the subject's anatomical space while simultaneously delivering both local anesthesia and a sling of the present invention. Accordingly, as the needle bodies are advanced into the anatomical spaces, trauma to surrounding tissue is minimized.

Figure 11:
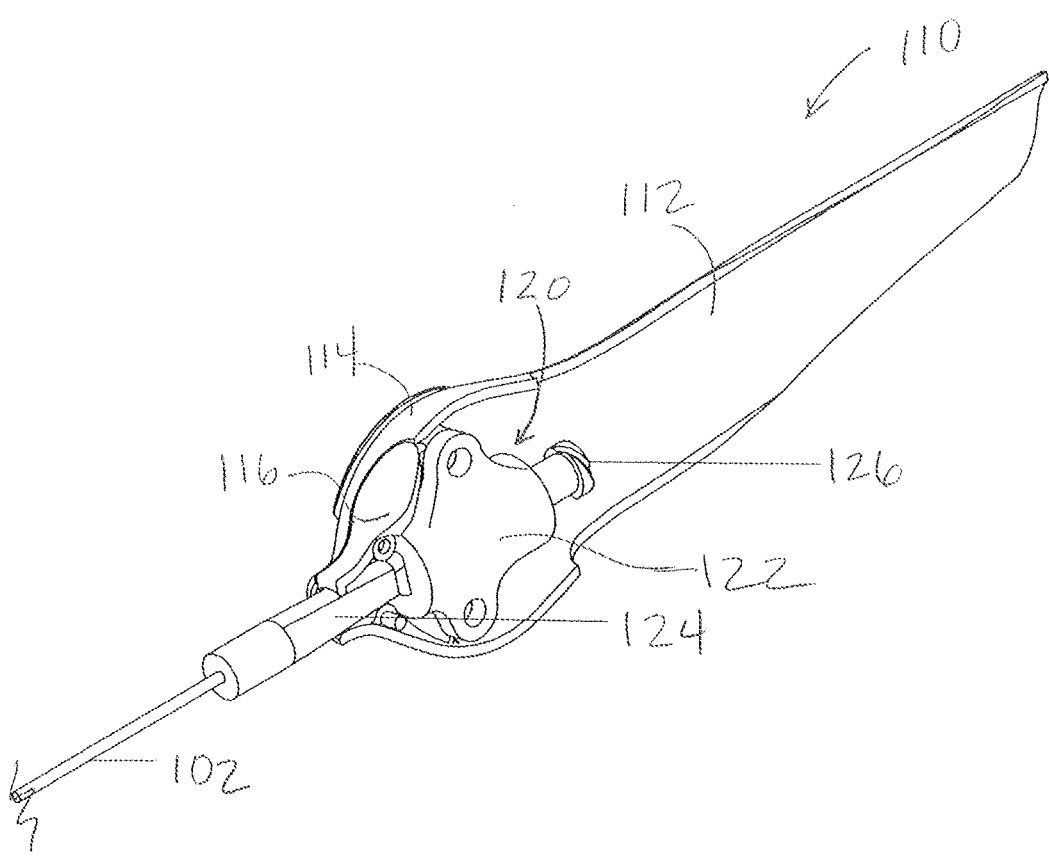
FIG. 11 depicts a perspective view of the handle of the needle delivery device of FIG. 9 and shown with a portion of its housing removed.

In a first example embodiment depicted in FIGS. 9-11, a needle delivery device 100 includes a needle body 102 having a sharp tip 104 at its distal end and having a lumen 106 extending through the length of the body. The tip 104 includes an aperture 108 therethrough that is sized and shape to accommodate a suture end of a sling of the present invention. As depicted, the body 102 is a generally elongated body with an arcuate, curved, or somewhat helical or spiral portion. Preferably, the body 102 is sized and shaped to allow a practitioner to navigate around the pubic ramus for the transobturator approach, or the pubic bone lateral to the symphysis for the retropubic approach.

The needle body 152 preferably includes three segments: a tip segment 103, a loop segment 105, and a proximal segment 107. Preferably, the tip segment 103 and the loop segment 105 form a continuous curvature loop that spans about 180° in the x-z plane. In alternative embodiments, the curvature of the loop can span about 120° to about 240° in the x-z plane. Preferably, the proximal segment 107 is a generally straight segment extending along the y-axis. Also preferably, the tip segment 103 is a generally straight segment extending along the x-axis, which is generally perpendicular to the y-axis.

Preferably, the needle body 102 and the tip 104 are fabricated from a biocompatible and rigid material, such as stainless steel, and can be generally smooth and polished on their exterior to facilitate penetration of soft tissue. In an example embodiment, the needle body has a gauge of between 10-25, although other suitable gauges of needle bodies can be employed as well. The length of the body 102 is preferably sufficient to reach from the subject's urethra to an insertion site at the skin (typically in either the groin or abdomen). Accordingly, the length of the needle body can be between approximately 3 cm to approximately 20 cm.

At the proximal end of the needle body 102 is a handle 110. Preferably, the handle 110 is an ergonomically shaped handle that provides a practitioner the ability to easily manipulate the needle delivery device with his hand. As shown in FIGS. 9 and 11, the handle 110 has a generally elongated body 112 having a generally bulbous member 114 at its proximal end. The bulbous member 114 can include one or more finger grips 116. An elongated slot 118 extends from the handle's distal end to the bulbous member 114.

Within the bulbous member 114, as shown more clearly in FIG. 11, is an assembly 120 for injecting a fluid through the needle body 102. The assembly 120 includes a receiver 122 for receiving a syringe 124 prefilled with fluid. The fluid can include, but is not limited to, a local anesthetic (e.g., lidocaine), another medication, or a saline solution. The syringe 124 includes a reservoir of fluid (not shown), a plunger 126 at one end, and a port (not shown) at the other that is in fluid communication with the lumen 106 of the needle body 102. Preferably, the coupling between the syringe's port and the lumen 106 prevents leakage. When depressed, the plunger 126 forces the fluid through the port and into the lumen 106 of the needle body 102. Optionally, a one way valve (not shown) can be located between the syringe's port and the needle's lumen 106 so as to prevent fluid in the needle's lumen from returning to the syringe's reservoir. The receiver 122 is mechanically coupled to the body 112 of the handle 110 (such as with fasteners) so as to retain the syringe 124 therein and to hold the port of the syringe in fluid communication with the lumen 106 of the needle body 102. Those skilled in the art will understand that the receiver 122 can be sized and shaped to accommodate a suitable syringe.

As shown, the plunger 126 of the syringe 124 somewhat extends beyond the wall of the slot 118 such that the practitioner can manipulate the handle 110 and depress the plunger with a thumb or finger. Accordingly, the practitioner can continuously control how much fluid is injected as he guides the needle body 102 through the anatomical space of the subject. In an alternative embodiment, the receiver includes a reservoir for housing a sufficient amount of fluid and a plunger for dispensing the fluid through a port of the reservoir. Thus in this embodiment, a separate syringe is not used.

Figure 13:
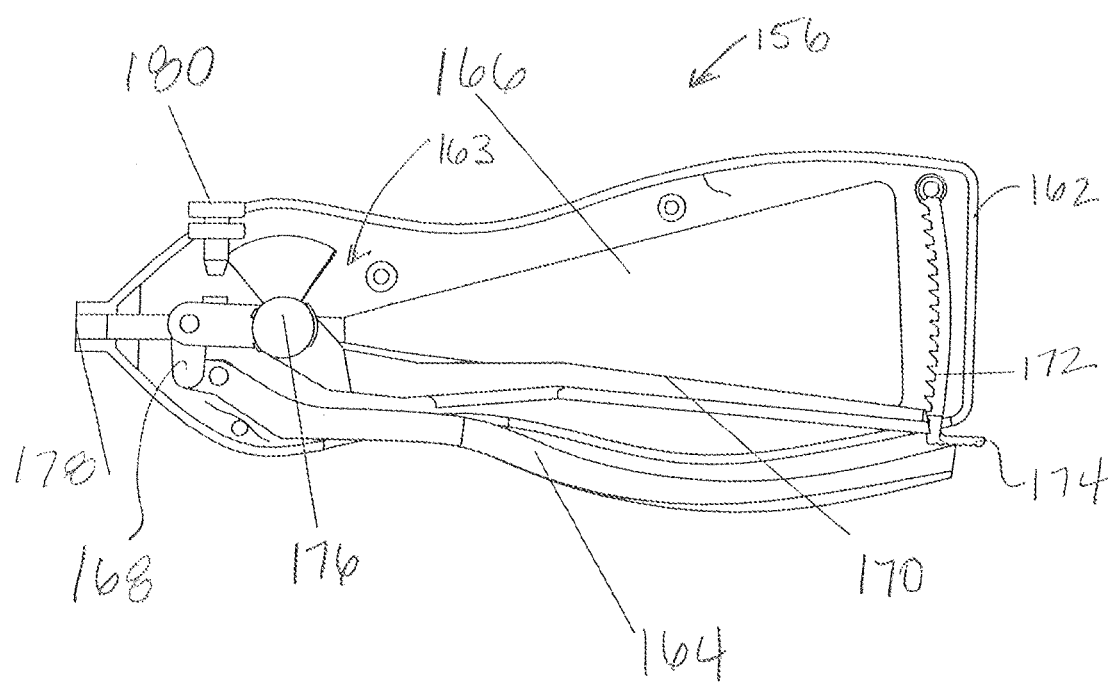
FIG. 13 depicts a sectional view of the handle of the needle delivery device of FIG. 12.

In another example embodiment as depicted in FIGS. 12-13, a needle delivery device 150 includes a generally helical or spiral shaped body 152, which is substantially similar to that shown in FIG. 9. The needle body 152 has a sharp tip 154 having a trigger-operated handle 156 to inject a fluid. Preferably, the diameter D of the curved/helical portion of the needle body 152 is approximately between 2 cm and 10 cm. The needle body 152 preferably includes three segments: a tip segment 153, a loop segment 155, and a proximal segment 157. Preferably, the tip segment 153 and the loop segment 155 form a continuous curvature loop that spans about 180° in the x-z plane and about 90° in the y-z plane. In alternative embodiments, the curvature of the loop can span about 120° to about 240° in the x-z plane. Preferably, the proximal segment 157 is a generally straight segment extending along the y-axis. Also preferably, the tip segment 153 is a generally straight segment extending along the x-axis, which is generally perpendicular to the y-axis.

Additionally, the needle body 152 and the tip 154 are fabricated from a biocompatible and rigid material, such as stainless steel, and can be generally smooth and polished on their exterior to facilitate penetration of soft tissue. Additionally, as shown in FIG. 12, the body 154 includes a lumen 158 and an aperture 160 at the tip 154.

FIG. 13 depicts the internal mechanics of the handle 156. The handle 156 includes a housing 162 and a dispensing assembly 163. The dispensing assembly 163 includes a user-operated trigger 164 extending through the housing and in communication with a fluid chamber or compartment 166. The trigger 164 provides the practitioner a way to release a fixed dosage or amount of medication (or other fluid) through the lumen 158 of the needle body 152. The trigger 164 is in mechanical communication with the fluid chamber 166. Preferably, the chamber 166 can be constructed of material that flexes or compresses. The trigger 164 is mechanically coupled through linkage 168 to a pivotal lever 170 that is locked in place with a toothed ratchet rack 172 (i.e., a generally linear ratchet rack). The ratchet rack 172 has a flanged end 174 protruding through the housing 162 of the handle 156 and engaged by the free end of the trigger 164. A user-operated button 176 coupled to the lever provides a release for permitting the lever 170 to advance in a backwards (or reverse) direction (so as to expand the chamber).

Thus, when the trigger 164 is activated, the lever 170 compresses the chamber 160 by a fixed amount and the end of the lever advances one tooth of the linear rack 172. In this sense, the end of the lever 170 functions like a pawl. As the chamber 166 is compressed, the fluid therein is forced out through the exit port 178 of the handle 156 and into the lumen 158 of the needle body 102 in a predetermined dosage. Each time the trigger 164 is activated, a predetermined dosage of fluid is released. In an alternative embodiment, the lever forms one wall of the chamber. Thus, as the lever advances, the chamber's volume becomes smaller.

In the depicted embodiment of FIGS. 12 and 13, the fluid chamber can be refilled. Preferably, the practitioner simultaneously presses the button 168 and pulls the flanged end 174 of the ratchet rack 172. In so doing, the dispensing assembly 163 is returned to its initial state where the chamber 166 is fully expanded. The practitioner can remove the stopper 180 from an opening of the handle, inject an adequate amount of fluid, and reattach the stopper. Optionally, a one way valve (not shown) can be located adjacent the exit port so as to prevent fluid in the needle's lumen from returning to the fluid chamber.

Figure 14:
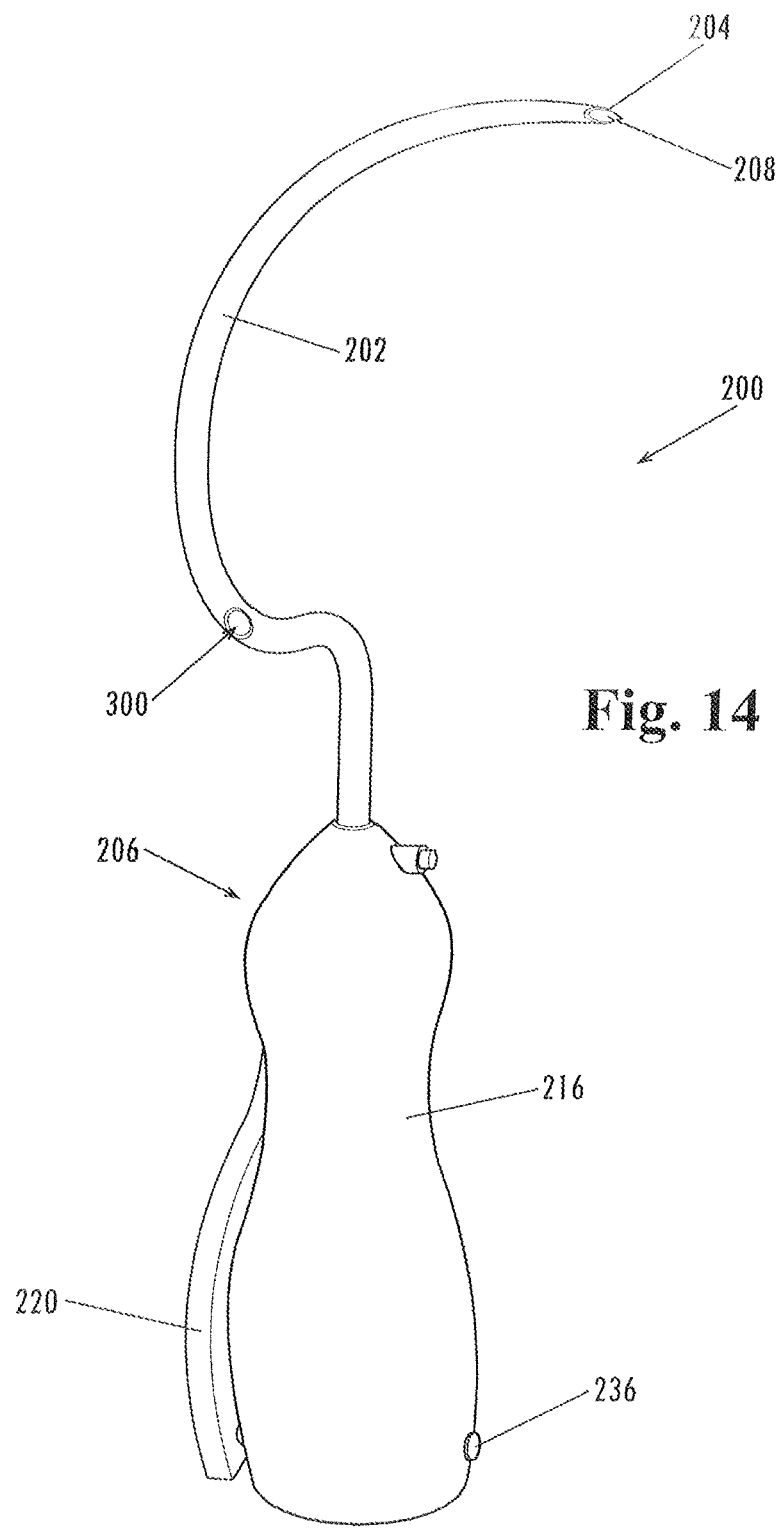
FIG. 14 depicts a perspective view of a needle delivery device for delivering a sling according to another example embodiment of the present invention.
Figure 15:
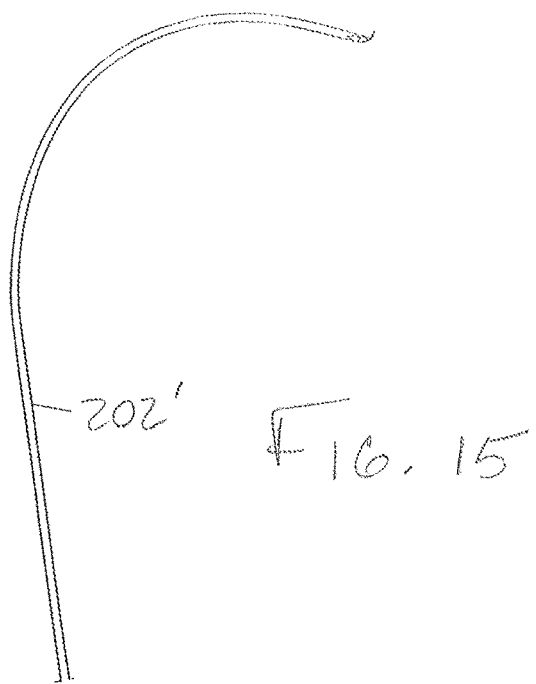
FIG. 15 depicts a perspective view of a needle body for delivering a sling according to another example embodiment of the present invention.
Figure 16:
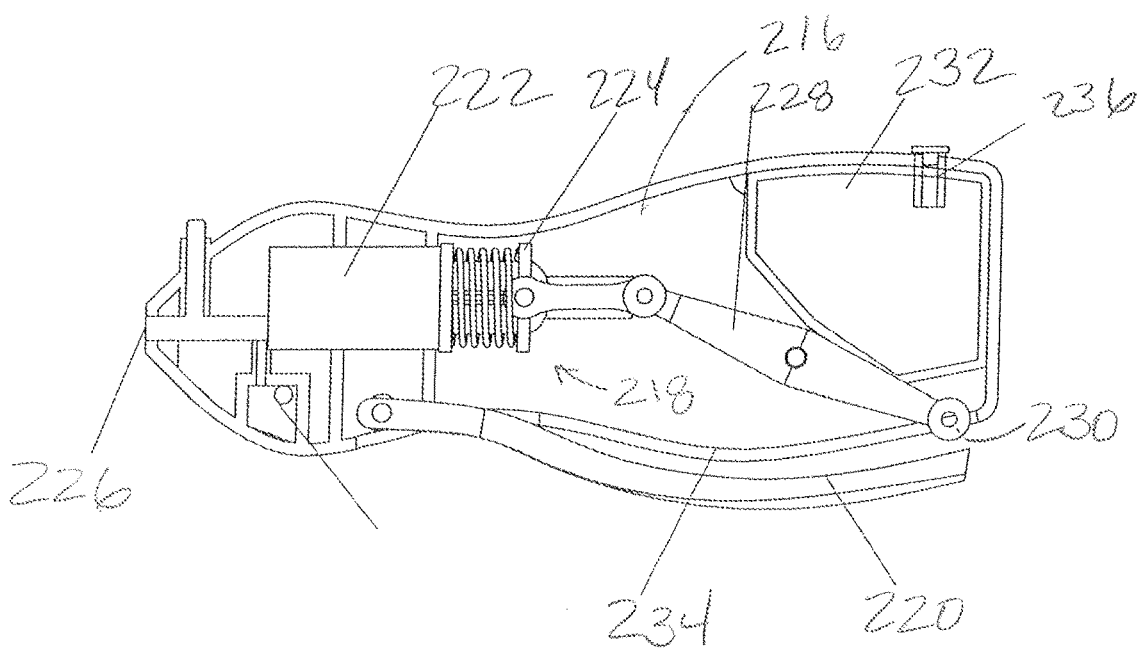
FIG. 16 depicts a sectional view of the handle of the needle delivery device of FIG. 14.

FIGS. 14 and 16 depict another example embodiment of a needle delivery device 200 of the present invention. The needle delivery device has a generally curved body 202 having a sharp tip 204 and a trigger-operated handle 206 to inject a fluid. Alternatively, the needle body 202' can be shaped/curved as shown in FIG. 15 (such as for use with a retropubic approach). Additionally, as shown in FIG. 14, the body 204 includes a lumen 208. The needle body 202 and tip 204 are constructed from suitable materials of suitable sizes as discussed above.

FIG. 16 depicts the inner mechanics of the handle 206. The handle 206 includes a housing 216 and a dispensing assembly 218. The dispensing assembly 218 includes a user-operated trigger 220 extending through the housing 216 and in communication with a fluid chamber or compartment 222. The fluid chamber 222 includes a piston 224 for dispensing the fluid out through the exit port 226. The piston 224 is coupled to mechanical linkage 228 having an end portion 230 extending through the housing 216. The end portion 230 is configured to be engaged by the trigger 220. Thus, activation of the trigger 220 engages the end portion 230 of the mechanical linkage 228 and causes the piston 224 to move into the fluid chamber 222, thereby dispensing a portion of the fluid therein through the exit port 226.

The fluid chamber 222 is further in fluid communication with a reservoir 232 containing additional fluid. The fluid chamber 222 can be coupled to the reservoir 232 with a tube 234. A one way valve (not shown) can be attached to the tube 234 so as to prevent fluid from returning to the reservoir 232. A second one way valve (not shown) can be located adjacent the exit port 226 so as to prevent fluid in the needle's lumen 208 from returning to the fluid chamber 222. To refill the reservoir 232, the practitioner removes the stopper 236, injects a suitable amount of fluid through the opening in the housing 216, and replaces the stopper.

Another example embodiment of a handle 250 is shown in FIG. 17. The handle 250 comprises a generally ergonomically shaped and substantially rigid housing 252 having an injection port 254 coupled to an exit port 256 near its distal end. A syringe 258 of fluid having an associated plunger 260 is coupled to the injection port 254. The exit port 256 is coupled to a needle body of the present invention such that the exit port is in fluid communication with the needle's lumen. Upon depression of the plunger 260, fluid flows from the syringe 258 through the injection port 254, out through the exit port 256, and into the lumen of the needle body. The injection port 254 and associated syringe 258 can be located at any suitable place along the housing.

Another example embodiment of a handle 270 is shown in FIG. 18. The handle 270 includes a substantially rigid housing 272 having an opening 274 for exposing a portion of a flexible reservoir 276. The handle 270 further includes an exit port 278 in fluid communication with a lumen of a needle body of the present invention. Upon depression of the flexible reservoir 276, fluid is forced out of the exit port 278 and into the lumen of the needle body. Although the reservoir 276 depicted in FIG. 18 is a flexible container housed within a rigid housing 272, the invention includes embodiments wherein a first portion of the housing can be substantially rigid while a second portion is substantially compressible. Still alternatively, the entire handle can be made of a flexible or compressible material such that as the handle is squeezed, fluid is forced out of the export port.

Any of the handles of the present invention can be combined with any of the needle bodies of the present invention, and the invention includes such embodiments.

Figure 19:
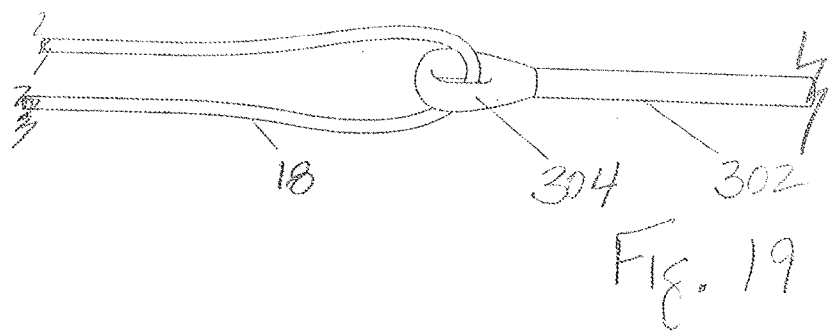
FIG. 19 depicts a perspective view of a portion of a guidewire for use with a needle of the present invention and shown receiving a suture end of a sling of the present invention.

Referring back to FIG. 14, the needle body 202 can include a small opening 300 in the wall that is sized and shaped to receive a guidewire 302 therethrough, as shown in FIG. 19. Preferably, the opening 300 is located near the handle 206, although the opening can be placed at any suitable location along the body 202. In such an embodiment, the practitioner can place his finger or thumb over the opening 300 when injecting the fluid so as to prevent the fluid from exiting the opening 300. Alternatively, the needle body can include two lumens, one for delivering the anesthesia and the other for delivering the sling. Alternatively or additionally, the opening in the needle body can include a flap for preventing fluid leakage therethrough.

Preferably, the guidewire 302 is constructed of a durable yet flexible material that can be threaded through the needle body. For example, the guidewire 302 can be constructed from a plastic or metal wire. In addition, the guidewire 302 can be placed through the tip 104 of a needle body (such as the needle delivery device 100 of FIG. 9) into the lumen 106 and out the opening 300. After passage of the guidewire 302, the needle body 102 can be removed and therefore the end of the guidewire can be fastened or otherwise secured to the sling 10 and/or suture 14, using the general principles of the Seldinger Technique.

As depicted in FIG. 19, the guidewire 302 can include an eyelet 304 at its distal end. Preferably, the eyelet has a size and shape that is suitable to receive a suture end of a sling of the present invention, such as suture end 18. Accordingly, the guidewire 302 can be inserted through the opening 300 (or tip end) of the needle body 202, into the lumen 208, and advanced to the needle's tip 204 (or to the opening 300). As the guidewire 302 is inserted into needle body 202, the eyelet 304 collapses, allowing it to be threaded through the needle body more easily. Preferably, the eyelet 304 of the guidewire 304 is inserted through the opening (or tip end)

first, although those skilled in the art will understand that the opposite end of the guidewire can be inserted through the opening or tip end.

Figure 20:
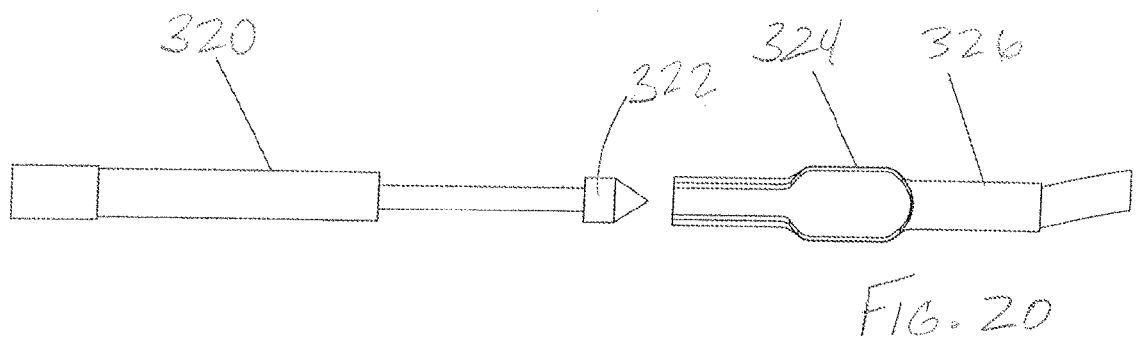
FIG. 20 depicts a side view of a guidewire and suture end of a sling according to another example embodiment of the present invention.
Figure 21:
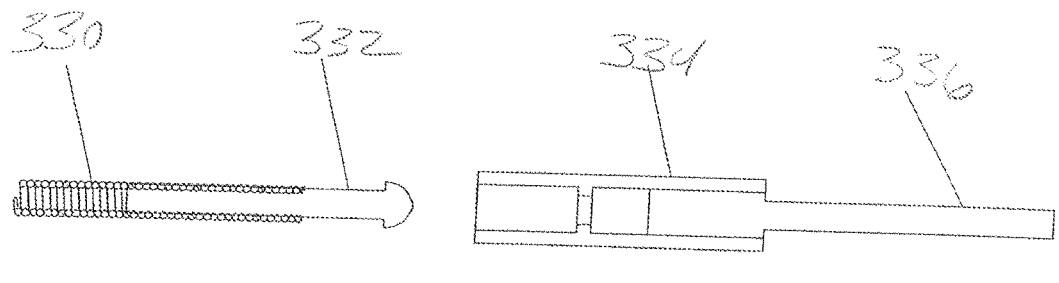
FIG. 21 depicts a side view of a guidewire and suture end of a sling according to yet another example embodiment of the present invention.

FIGS. 20-24 depict several guidewires according to various example embodiments of the present invention. Each of the guidewires includes an attachment feature for securely grasping a suture end of the sling of the present invention. For example in FIG. 20, the guidewire 320 includes an anchor 322 at a distal end thereof that can mate with a coopering portion 324 of a suture end 326 of a sling of the present invention. As shown in FIG. 20, the cooperating portion 324 can include an anchor seat in which the anchor is securely housed. Once the guidewire 320 and suture end 326 are pulled through a needle body of the present invention and the sling is at least somewhat around the urethra or in an otherwise appropriate placement, the practitioner can disengage the guidewire from the suture end by pulling the two apart. FIG. 21 depicts a guidewire 330 according to an alternative embodiment having an anchor 332 that mates with an anchor seat 334 of a suture end 336 of a sling. Although the anchors are described as being a part of the guidewire, in an alternative embodiment, the anchors can be a part of the suture end.

In FIGS. 22 and 23, a suture end 340 of the sling includes a threaded female member 342 attached thereto. A guidewire 344 can include a cooperating threaded end 346 that mates with the threaded female member of the suture end. Once the guidewire 344 and suture end 340 are pulled through a needle body of the present invention and the sling is at least somewhat around the urethra or otherwise in appropriate placement, the practitioner can cut the suture end to remove the threaded female member or can otherwise disengage the threaded female member from the suture end. Although the threaded female member is described as being a part of the suture end, in an alternative embodiment, the threaded female member can be a part of the guidewire.

In FIG. 24, a guidewire 350 includes a clamp 352 for securely gripping a suture end 354 of a sling of the present invention. The suture 354 end can be inserted into the clamp 352, and the clamp can be closed (by squeezing the clamping members together). Once the guidewire 350 and suture end 354 are pulled through a needle body of the present invention and the sling is at least somewhat around the urethra (or otherwise placed in an appropriate placement), the practitioner can disengage the suture end 354 from the guidewire 350 by opening the clamp 352 and releasing the suture end. Although the clamp is described as being a part of the guidewire, in an alternative embodiment, the clamp can be a part of the suture end.

FIG. 25 depicts a finger guard 360 for use with the needle delivery devices of the present invention. The finger guard is sized and shaped to cover at least a fingertip (or thumbtip) of the practitioner. Preferably, the finger guard 360 is constructed from a puncture resistant material, such as ballistic nylon, although other suitable materials can be employed as well. In use, the practitioner places the finger guard 360 over one his fingers or thumbs. Thus, as the practitioner is guiding a needle body from a point external to the subject's body to an area of a premade incision, the practitioner can feel the placement of the sharp tip of the needle without risking being injured.

In use, a practitioner uses a pair of needle delivery devices of the present invention to implant a sling of the present invention in appropriate placement (such as around a subject's urethra) while using the same needle delivery devices to simultaneously deliver a local anesthetic along the insertion tract. The following method is described in terms of the sling 10 of FIG. 1 and the needle delivery device 100 of FIGS. 9-11. However, those skilled in the art will understand that any of the slings and needle delivery devices of the present invention can be employed and be within the scope of the present invention.

When implanting the sling 10 in a female subject in a first example embodiment, the practitioner initially applies a local anesthetic and makes a small incision or stab wound in the vaginal area. The practitioner threads the first suture end 18 of the sling 10 through the aperture 108 of the first needle delivery device 100 and the second suture end 20 of the sling through the aperture 108 of the second needle delivery device. The practitioner inserts the first and needle delivery devices 100, each carrying a portion of the sling 10, through the vaginal incision. The practitioner injects the local anesthetic from the handle reservoirs by depressing the plungers 126 as he advances the needles 100 behind the pubic ramus and generally in a direction towards an appropriate area of groin skin or suprapubic region.

Alternatively if a needle is used having an aperture at a location other than the tip of the needle such as needle 200, once the tips 208 of the needles protrude through the skin in the groin or suprapubic region, the practitioner threads a guidewire, such as guidewire 302 into the lumen 208 at the tip 204 of the first needle 200. When the eyelet 304 of the guidewire 302 is located near the vaginal incision, the practitioner holds the eyelet while removing the needle 200 from the subject's body. The steps of threading the guidewire through the needle and removing the needle from the body are repeated for the second needle. Thus, the two eyelets 304 of the two guidewires 302 are now located near the vaginal incision. The practitioner threads the first suture end 18 of the sling 10 through the eyelet 302 of the first guidewire 304 and the second suture end 20 of the sling through the eyelet of the second guidewire and then pulls the guidewires and hence the sling into placement.

Regardless of whether the practitioner uses the needles or guidewires to pull the sling, the practitioner manipulates the proximal ends of the needle delivery devices or guidewires so as to remove the needles or guidewires from the subject through the reverse path. Once the needles (or guidewires) exit the body, the practitioner removes the suture ends from the needles (or guidewires) and positions the intermediate portion 26 of the sling underneath the urethra and positions the adjustment loop 22 accordingly. The practitioner adjusts the tension on the sling, cuts the suture ends to about 5 cm long, and secures the suture ends to the subject at a point external to the subject's body. For example, the suture ends 18, 20 can be secured beneath suitable bandages, such as TAGADERM™ dressings. Before closing the incision in the vaginal wall, the practitioner can either superficially bury the loop 22 of the sling 10 in the incision or can close the incision in such a manner that at least a portion of the loop 22 protrudes through the incision for adjusting the tension of the sling 10 after the procedure.

Within about 24-48 hours after the procedure, the practitioner can readjust the sling 10. The slings of the present invention can be adjusted up to about seven days or so after the procedure. Optionally, the practitioner can use a urethral dilator to provide counter-traction. The practitioner removes the bandages covering the suture ends 18, 20 and manipulates the suture ends and/or loop 22 of the sling 10 (currently located near the site of the vaginal incision). Pulling on the suture loop 22 loosens the sling 10 around the urethra, while pulling on the suture ends 18, 20 tightens the sling around the urethra. Once proper tensioning is established, the practitioner trims suture ends at skin level and cuts the adjustment loop at the midline vaginal incision.

Figure 26:
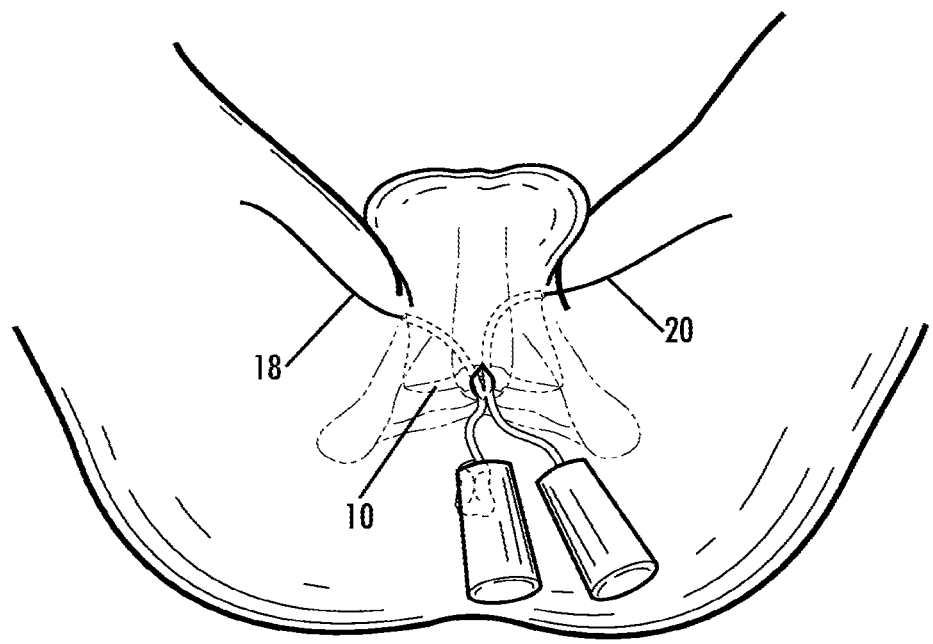
FIGS. 26-27 depict pictorial representations of a pair of needle delivery devices of the present invention used to implant a sling of the present invention in a male subject.

When implanting the sling 10 in a male subject, the subject is first placed in a high lithotomy position. A Foley catheter is placed through the subject's urethra and into his bladder. The practitioner applies a local anesthetic such as lidocaine and makes a small incision or midline stab wound in the perineum. The practitioner creates subcutaneous spaces with metzenbaum scissors, lateral to the midline urethra on each side. The practitioner inserts the first needle body 102 through the perineal incision, and passes the needle body 102 through the obturator foramen, to the appropriate area on the subject's groin. The second needle body is passed on the contralateral side, as shown in FIG. 26. The practitioner injects the local anesthesia from the handle reservoirs by depressing the plungers 126 as he advances the needles from inside the perineal incision, through the obturator foramen, and out at the ipsilateral groin. Prior to passage of each needle, the practitioner threads the suture ends 18, 20 of the sling 10 through the aperture 108 of each needle body 102; thus, the suture 14 is carried, as anesthetic is simultaneously delivered, along this tract leading up to the groin. Once the tips 104 of the needles 100 protrude through the groin skin, the suture ends 18, 20 are freed from the needles, and the needles are removed through the perineal incision, leaving only the sling body (e.g., mesh) and suture ready for tensioning.

Alternatively, if a needle is used having an aperture at a location other than the tip of the needle such as needle 200, once the tips 204 of the needles 200 protrude through the groin skin, the practitioner threads a guidewire from outside the groin skin, such as guidewire 302, through the aperture 300 of the first needle. When the eyelet 304 of the guidewire 302 exits near the incision in the perineal wall, the practitioner holds the eyelet while removing the needle from the subject's body. The steps of threading the guidewire through the needle and removing the needle from the body are repeated for the second needle. Thus, the two eyelets 304 of the two guidewires 302 are now located near the perineal incision. The practitioner threads the first suture end 18 of the sling 10 through the eyelet 304 of the first guidewire 302 and the second suture end 20 of the sling through the eyelet of the second guidewire.

Figure 27:
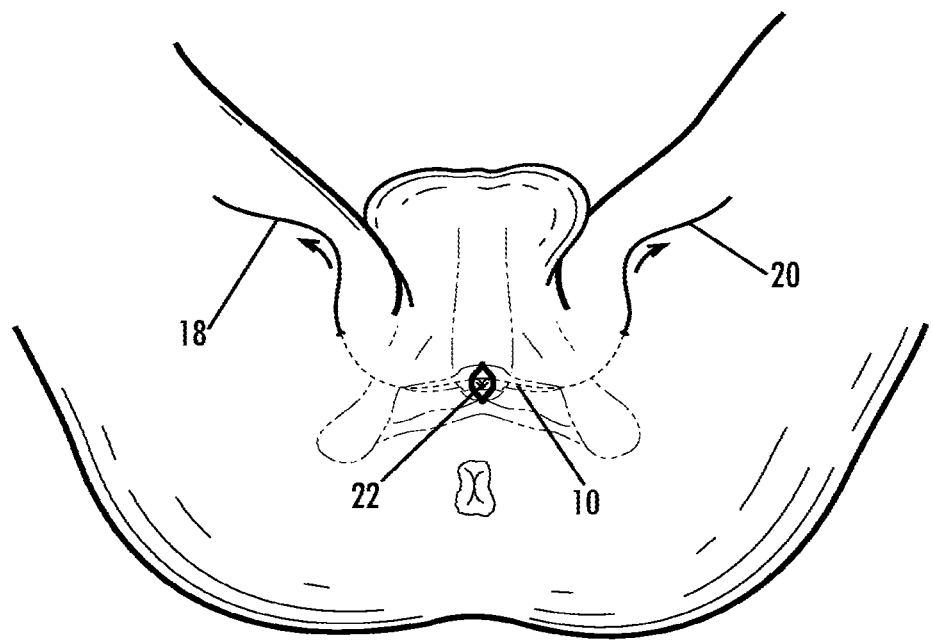

Regardless of whether the practitioner uses the needles or guidewires to pull the sling, the practitioner manipulates the proximal ends of the needle delivery devices or guidewires so as to remove the needle bodies or guidewires from the subject through the reverse path. The practitioner positions the intermediate portion 26 of the sling underneath the urethra and/or the perineal body and positions the adjustment loop 22 accordingly, as generally shown in FIG. 27. Once the needles (or guidewires) exit the subject's body, the practitioner removes the suture ends 18, 20 from the needles (or guidewires) and adjusts the tension and placement of the sling. For example, the practitioner can ask the subject to cough (or otherwise engage the subject in an activity that causes intraabdominal pressure) as he is adjusting the tension of the sling 10. The practitioner cuts the suture ends 18, 20 to about 5 cm long and secures the suture ends to the subject at a point external to the subject's body. For example, the suture ends 18, 20 can be secured beneath suitable bandages, such as TAGADERM™ dressings. The practitioner can place a steristrip or suture over the stab wound in the perineal wall such that a portion of the adjustment loop 22 extends through the wound.

Within about 24-48 hours or up to a week or so after the procedure, the practitioner can readjust the sling 10, after the patient has assessed its efficacy and voiding function during activities. The practitioner removes the bandages covering the suture ends 18, 20 and manipulates the suture ends and/or loop 22 of the sling 10 at the site of the perineal incision. Pulling on the suture loop 22 loosens the sling 10 around the urethra, while pulling on the suture ends 18, 20 tightens the sling around the urethra. To aid in the adjustment of the tensioning, the practitioner can ask the subject to cough (or otherwise engage the subject in an activity that causes intraabdominal pressure) as he is adjusting the tension of the sling 10. Once proper tensioning is established, the practitioner trims suture ends 18, 20 at skin level and cuts the adjustment loop at the midline vaginal incision.

Although the present invention is described in terms of "inside-out" methods of implanting slings in female and male subjects, the methods of the present invention can be adapted to provide "outside-in methods" for both female and male subject and be within the scope of the present invention. For example, the practitioner can insert the first needle body 102 through a female subject's abdomen or groin and the second needle body 102 through the subject's abdomen or groin. The practitioner can inject the local anesthetic from the handle reservoirs by depressing the plungers 126 as he advances the needle bodies 102 generally in a direction towards the premade vaginal incision. Once the tips 104 of the needles protrude through the vaginal incision, the practitioner can thread the first suture end 18 of the sling 10 through the aperture 108 of the first needle and the second suture end 20 of the sling through the aperture 108 of the second needle. The practitioner can manipulate the proximal ends of the needle delivery devices so as to remove the needle bodies the subject through the reverse path. In so doing, the practitioner is simultaneously pulling the suture ends 18, 20 of the sling 10 through the passages initially created by the needles as the needles are removed from the subject's body.

Additionally, other suitable methods of implanting the sling can be used and be within the scope of the present invention.

In another form, the present invention provides a kit for the treatment of urinary incontinence. The kit can include one, and preferably two, needle delivery devices of the present invention, a sling of the present invention, and a finger guard of the present invention. Optionally, the kit can include one or more syringes or vials of local anesthetic, one or more bandages, and one or more guidewires of the present invention.

While the invention has been described with reference to preferred and example embodiments, it will be understood by those skilled in the art that a variety of modifications, additions and deletions are within the scope of the invention, as defined by the following claims.

The invention claimed is:

1. An apparatus for the treatment of stress urinary incontinence, comprising:
  a sling body having a first end portion, a second end portion, and an intermediate portion disposed between the first end portion and the second end portion, the intermediate portion having a first surface portion and a second surface portion opposite the first surface portion, the intermediate portion having a width that is larger than a width of the first end portion, the width of the intermediate portion being larger than a width of the second end portion; and
  a suture extending through the sling body, the suture being woven through the first end portion and the second end portion, the suture extends across the first surface portion of the intermediate portion with an adjustment loop extending through an opening and protruding from the second surface portion, the adjustment loop having a size larger than any loops formed by the suture being woven through the first end portion and the second end portion.

2. The apparatus of claim 1, wherein the suture has a first free end and a second free end, the first free end extending from a terminal end of the first end portion, the second free end extending from a terminal end of the second end portion.

3. The apparatus of claim 2, wherein the first free end is at least 5 cm long.

4. The apparatus of claim 1, wherein the suture is secured to the sling body with a plurality of knots.

5. The apparatus of claim 1, wherein the suture is bioabsorbable.

6. The apparatus of claim 1, wherein the sling body is constructed of a surgical mesh material.

7. The apparatus of claim 1, wherein the sling body is symmetrically shaped about a longitudinal axis of the sling body, and the sling body is symmetrically shaped about a transverse axis of the sling body.

8. The apparatus of claim 1, wherein the intermediate portion has a different shape than either the first end portion or the second end portion.

9. The apparatus of claim 8, wherein the width of the intermediate portion is in a range of 10 mm to 40 mm, and the width of the first end portion and the second end portion is in a range of 5 mm to 10 mm.

10. The apparatus of claim 1, wherein the adjustment loop is configured to adjust a tension of the sling body postoperatively.

11. A needle delivery device for implanting a medical device, comprising:
a needle body including an aperture configured to receive a suture end of the medical device;
a lumen extending through a length of the needle body, the lumen configured to deliver a fluid therethrough; and
a handle coupled to the needle body, the handle including a housing, and a trigger movably coupled to the housing, the housing including a flexible fluid chamber configured to store fluid within, and a lever configured to compress the flexible fluid chamber and dispense the fluid, the trigger operatively coupled to the lever.

12. The needle delivery device of claim 11, wherein the handle includes a supply of local anesthetic in fluid communication with the lumen.

13. The needle delivery device of claim 11, wherein the needle body includes a tip segment, a loop segment, and a straight proximal segment, the tip segment and the loop segment being disposed in a plane orthogonal to a longitudinal axis of the straight proximal segment.

14. The needle delivery device of claim 11, wherein the aperture is located proximate the handle.

15. The needle delivery device of claim 11, wherein the needle body includes a beveled tip, and the aperture extends through the beveled tip.

16. A method for implanting a sling to treat urinary incontinence in a human or animal subject, comprising:
making an incision in a perineal or vaginal area;
inserting first and second needles,
each of the first and second needles carrying a portion of the sling into the human or animal subject;
guiding the first and second needles carrying the sling to an appropriate site in a groin or suprapubic area while simultaneously injecting local anesthesia through the first and second needles;
removing the first and second needles;
positioning the sling; and
leaving at least a portion of the sling accessible for post-operative adjustment of the sling.

17. The method of claim 16, wherein the sling includes a suture having two free ends and wherein the step of leaving at least a portion of the sling accessible for post-operative adjustment of the sling further includes leaving the two free ends of the suture external to the subject's body.

18. The method of claim 16, wherein the sling includes a suture having an adjustment loop and wherein the step of leaving at least a portion of the sling accessible for post-operative adjustment of the sling further includes leaving the adjustment loop accessible.

19. The method of claim 16, further comprising adjusting a tension of the sling postoperatively by manipulating the accessible portion of the sling.

20. A kit for the treatment of urinary incontinence, comprising:
a suburethral sling;
a pair of delivery needles, wherein each delivery needle is configured to deliver local anesthesia to the suburethral sling around a urethra;
a guidewire member configured to grasp a suture end of the suburethral sling, the guidewire member configured to be inserted into an opening of at least one of the pair of delivery needles; and
a finger guard having an open end, a closed end, and a cavity that extends into the finger guard from the open end, the finger guard configured to encompass a fingertip of a practitioner, the finger guard including a flexible puncture resistant material, wherein the suburethral sling, the pair of delivery needles, and the finger guard are packaged together in the kit.

21. The kit of claim 20, wherein the guidewire member includes an anchor at a distal end thereof so as to engage the suture end of the suburethral sling.

* * * * *